United States Patent [19]

Von der Crone

[11] 3,994,921

[45] Nov. 30, 1976

[54] IMINOISOINDOLENINE PIGMENTS, PROCESS FOR THEIR MANUFACTURE AND THEIR USE

[75] Inventor: Jost Von der Crone, Riehen, Switzerland

[73] Assignee: Ciba-Geigy Corporation, Ardsley, N.Y.

[22] Filed: Oct. 21, 1975

[21] Appl. No.: 624,345

[30] Foreign Application Priority Data

Oct. 30, 1974 Switzerland................. 14526/74

[52] U.S. Cl. ................ 260/326.1; 260/37 P; 260/39 P; 260/40 TN; 106/23; 106/288 Q
[51] Int. Cl.² ........................... C07D 209/44
[58] Field of Search .................... 260/326.1

[56] References Cited
UNITED STATES PATENTS 3,758,497   9/1973   Pugin et al................. 260/326.1

FOREIGN PATENTS OR APPLICATIONS 945,782   7/1956   Germany.................... 260/326.1
2,322,777   11/1973   Germany.................... 260/326.1

*Primary Examiner*—Elbert L. Roberts
*Assistant Examiner*—S. P. Williams
*Attorney, Agent, or Firm*—Vincent J. Cavalieri

[57] ABSTRACT

Iminoisoindolenine pigments of the formula

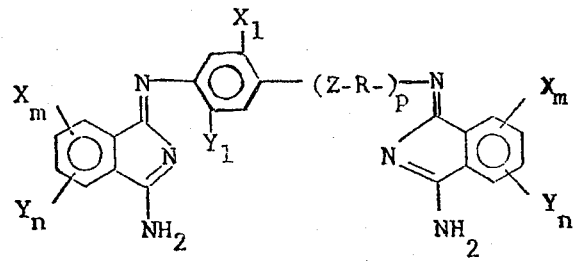

wherein R represents a phenylene or diphenylene radical, X represents a hydrogen or halogen atom, Y represents an alkyl, alkoxy, alkanoylamino or alkylsulphonyl group containing 1 to 4 carbon atoms, a nitro group, a phenyl, benzoylamino, phenoxy or phenylsulphonyl group which may be substituted by halogen atoms, alkyl or alkoxy groups of 1 to 4 carbon atoms, $X_1$ represents a hydrogen or halogen atom, an alkyl or alkoxy group of 1 to 4 carbon atoms, an alkoxycarbonyl group of 2 to 6 carbon atoms, a nitro, trifluoromethyl, carbamoyl or cyano group, $Y_1$ represents a halogen atom, an alkyl or alkoxy group of 1 to 4 carbon atoms or a trifluoromethyl group, Z represents a —NHCO or NHCONH group, $m$ is 1 to 4, $n$ is 0 to 2, and $p$ is 0 to 1, the sum of $m + n$ being 4, are useful for coloring plastics and lacquers in yellow shades of excellent fastness properties.

3 Claims, No Drawings

IMINOISOINDOLENINE PIGMENTS, PROCESS FOR THEIR MANUFACTURE AND THEIR USE

The present invention provides new iminoisoindolenine pigments of formula

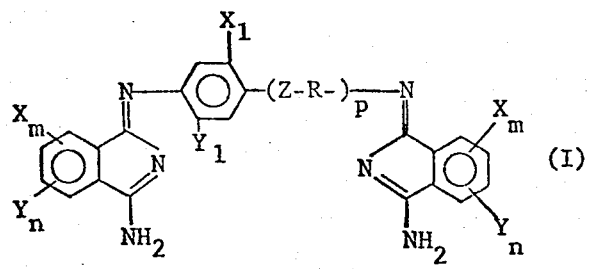

wherein R represents a phenylene or diphenylene radical, X represents a hydrogen or halogen atom, Y represents an alkyl, alkoxy, alkanoylamino or alkylsulphonyl group containing 1 to 4 carbon atoms, a nitro group, a phenyl, benzoylamino, phenoxy or phenylsulphonyl group which is substituted by halogen atoms, alkyl or alkoxy groups of 1 to 4 carbon atoms, or is unsubstituted, $X_1$ represents a hydrogen or halogen atom, an alkyl or alkoxy group containing 1 to 4 carbon atoms, an alkoxycarbonyl group of 2 to 6 carbon atoms, a nitro, trifluoromethyl, carbamoyl or cyano group, $Y_1$ represents a halogen atom, an alkyl or alkoxy group of 1 to 4 carbon atoms or a trifluoromethyl group, Z represents a —NHCO or —NHCONH group, m is 1 to 4, n is 0 to 2 and p is 0 to 1, the sum of $m + n$ being 4.

It is possible that the pigments of the present invention are also in the tautomeric form

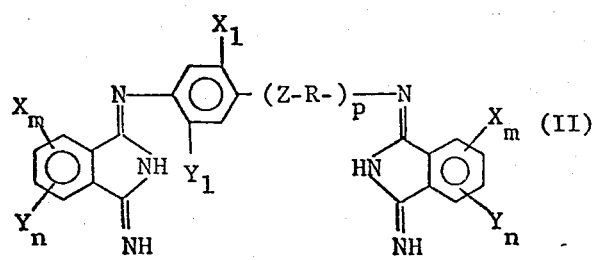

Preferred pigments are those of formula I, wherein X represents a hydrogen atom, $X_1$ represents a chlorine or bromine atom and $Y_1$ represents a chlorine or bromine atom, a methyl, methoxy or ethoxy group and m is 4, and in particular those wherein $X_1$ and $Y_1$ represent chlorine atoms.

Particularly interesting pigments are those of formula

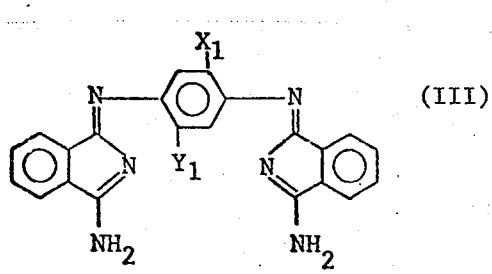

wherein $X_1$ and $Y_1$ are as defined hereinbefore, preferably those wherein $X_1$ represents a chlorine or bromine atom and $Y_1$ represents a chlorine or bromine atom or a methyl group, and of especial interest is the pigment of formula

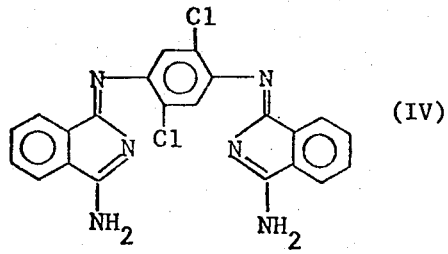

The pigments of the present invention are obtained by condensing an aminoiminoisoindolenine of formula

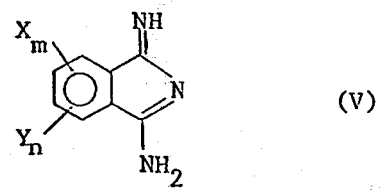

or a phthalonitrile of formula

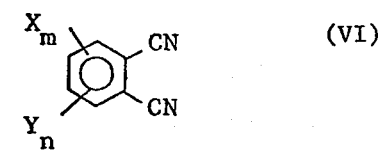

in the molar ratio 2:1, with a diamine of formula $$H_2N-\text{(Z-R)}_p-NH_2 \quad (VII)$$

A start is advantageously made from an aminoiminoisoindolenine of formula (V), wherein X and Y represent hydrogen atoms, i.e. from 1-amino-3-iminoisoindolenine.

Further examples of aminoiminoisoindolenines are:
1-amino-3-imino-4-chloro-isoindolenine
1-amino-3-imino-5,6-dichloro-isoindolenine
1-amino-3-imino-5-methyl-isoindolenine
1-amino-3-imino-5-methoxy-isoindolenine
1-amino-3-imino-5-ethoxy-isoindolenine
1-amino-3-imino-5-phenoxy-isoindolenine
1-amino-3-imino-5-acetylamino-isoindolenine
1-amino-3-imino-5-benzoylamino-isoindolenine
1-amino-3-imino-5-methylsulphonyl-isoindolenine
1-amino-3-imino-5-phenylsulphonyl-isoindolenine
1-amino-3-imino-5-nitro-isoindolenine
1-amino-3-imino-5-phenyl-isoindolenine
1-amino-3-imino-5,6-diphenyl-isoindolenine These aminoiminoisoindolenines are known compounds which are obtained by the process of German Pat. No. 879,100 by reacting the phthalonitriles of formula (VI) with ammonia or derivatives thereof.

The pigments of this invention can also be manufactured direct by starting from the phthalonitriles of formula (VI), in which process the 1-alkoxy-3-iminoisoindolenines are formed as intermediates.

Examples of phthalonitriles are:
phthalonitrile
3-chloro-phthalonitrile
3,4-dichloro-phthalonitrile
4-methyl-phthalonitrile
4-methoxy-phthalonitrile
4-ethoxy-phthalonitrile
4-phenoxy-phthalonitrile
4-acetylamino-phthalonitrile
4-benzoylamino-phthalonitrile
4-methylsulphonyl-phthalonitrile
4-phenylsulphonyl-phthalonitrile
4-nitro-phthalonitrile
4-phenyl-phthalonitrile
4,5-diphenyl-phthalonitrile As diamines there are used preferably those of formula (VII), wherein $X_1$ represents a chlorine or bromine atom and $Y_1$ represents a chlorine or bromine atom, a methyl, methoxy or ethoxy group, and, in particular, those of formula

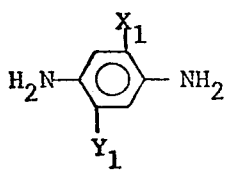

A particularly preferred diamine is 2,5-dichloro-1,4-phenylenediamine.

Examples of further diamines are:
2-chloro-1,4-phenylenediamine
2-bromo-1,4-phenylenediamine
2-iodo-1,4-phenylenediamine
2-fluoro-1,4-phenylenediamine
2-methyl-1,4-phenylenediamine
2-methoxy-1,4-phenylenediamine
2-ethoxy-1,4-phenylenediamine
2-nitro-1,4-phenylenediamine
2-trifluoromethyl-1,4-phenylenediamine
2-cyano-1,4-phenylenediamine
2-methoxycarbonayl, 1,4-phenylenediamine
2-carbamoyl-1,4-phenylenediamine
2,5-dichloro-1,4-phenylenediamine
2,5-dibromo-1,4-phenylenediamine
2,5-dimethyl-1,4-phenylenediamine
2,5-dimethoxy-1,4-phenylenediamine
2,5-diethoxy-1,4-phenylenediamine
2,5-bis-trifluoromethyl-1,4-phenylenediamine
2-chloro-5-methyl-1,4-phenylenediamine
2-chloro-5-methoxy-1,4-phenylenediamine
2-chloro-5-ethoxy-1,4-phenylenediamine
2-methyl-5-methoxy-1,4-phenylenediamine
2-methyl-5-ethoxy-1,4-phenylenediamine These diamines are known compounds. The bicyclic diamines of formula

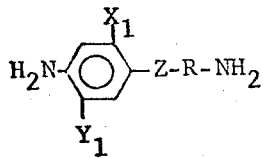

are obtained by condensing an aminonitrobenzene of formula

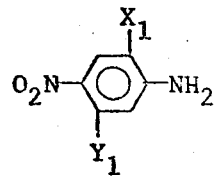

with a nitrobenzenecarboxylic acid chloride or a nitrodidiphenylcarboxylic acid chloride or with a nitrophenylor nitrodiphenylisocyanate and reduction of the resultant dinitro compound.

Examples of bicyclic diamines are:
4,4'-diamino-2,5-dichloro-benzanilide
4,4'-diamino-2,5-dimethyl-benzanilide
4,4'-diamino-2,5-dimethoxy-benzanilide
4,4'-diamino-2-chloro-5-methyl-benzanilide
4,4'-diamino-2-chloro-5-methoxy-benzanilide
4,4'-diamino-2-methyl-5-methoxy-benzanilide
4,3'-diamino-4',2,5-trichloro-benzanilide
4,3'-diamino-2,5-trichloro-4'-methoxy-benzanilide
4,3'-diamino-2,5-trichloro-4'-methyl-benzanilide
4,3'-diamino-2,5,2',4'-tetrachloro-benzanilide
4-amino-2,5-dichloro-4'-(4''-aminophenyl)-benzanilide
bis-N,N'-(4-amino-2,5-dichlorophenyl)-urea The condensation of the compound of formula V or VI with the diamine takes place partly at low temperature, if appropriate with heating of the intimately mixed components, with particular advantage in the presence of inert organic solvents, i.e. solvents that do not participate in the reaction. It is advantageous to use water-miscible organic solvents, for example lower aliphatic alcohols, such as lower alkanols, for example methanol, isopropanol or butanol, lower cyclic ethers, for example dioxan, ethylene glycol monomethyl ether, lower aliphatic ketones, for example acetone or carboxy amides, for example formamide. The condensation takes place at relatively low temperatures. It is advantageous to carry out the process in the presence of an alkali agent, for example a lower fatty acid, which can then be used simultaneously as solvent, in particular acetic acid.

Immediately after its formation, the new pigment falls out of the reaction medium. It can be used for certain purposes as crude pigment direct; but it is advantageous to condition it before application by known methods, for example by extraction with an organic solvent or by grinding with grinding assistants which can afterwards be removed again, for example salts or, in particular, hexachloroethane, or by precipitation with alkali. The purity, intensity and transparency are thereby improved.

The new colourants are useful pigments which, in finely divided form, can be used for pigmenting organic material of high molecular weight, for example cellulose ethers and esters, such as ethyl cellulose, acetyl cellulose or nitrocellulose, polyamides, polyurethanes or polyesters, natural or synthetic resins, for example aminoplasts, especially thermoplastic and curable acrylic resins, phenolic plastics, polycarbonates, polyolefins, for example polystyrene, polyvinyl chloride, polyethylene, polypropylene, polyacrylonitrile, polyacrylic esters, rubber, casein, silicon and silicone resins, singly or in mixtures. It is immaterial whether these compounds of high molecular weight are in the form of plastics, melts, spinning solutions, varnishes, paints or printing inks. Depending on the use to which they are put, it is advantageous to use the pigments of the present invention as toners or in the form of preparations.

The pigments of this invention are characterised by excellent fastness properties, in particular by outstanding fastness to light, migration and weathering, as well as by high colour strength, high gloss, good dispersibility and heat resistance. Surprising too is their good resistance to acids.

Compared with the pigments described in German Offenlegungsschrift 2,322,777, the pigments of the present invention are characterised by a greater colour strength and by better light and weather fastness. German Pat. No. 945,782 describes similar compounds which are obtained by condensing 2 moles of phthalonitrile with 1 mole of m-phenylenediamine. However, these products are only useful as intermediates, since they are not heat-resistant. When heated in inert organic solvents at temperatures between 150° and 200° C, they split off ammonia with ring closure. In contradistinction thereto, the pigments of the present invention are characterised by good heat-resistance.

The following Examples illustrate the invention, the percentages being by weight.

EXAMPLE 1

With stirring, 15.5 g of 1-amino-3-imino-isoindolenine and 5.3 g of 2,5-dichloro-1,4-phenylenediamine are heated to 80° C in 150 ml of glacial acetic acid. A yellow crystalline precipitate separates and is filtered off after 30 minutes. It is washed with methanol, acetone and water and dried.

Yield: 10.3 g (=79% of theory).

The following constitution can be assumed from the analytical values:

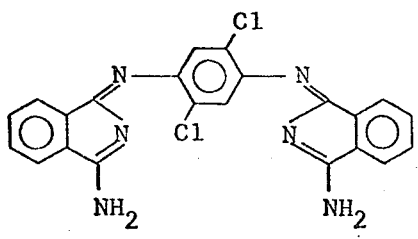

|  | C | H | Cl | N |
|---|---|---|---|---|
| found | 60.6 | 3.13 | 16.4 | 19.0 |
| estimated | 60.97 | 3.13 | 16.40 | 19.40 |

The product can be used direct as pigment. Polyvinyl chloride sheets can be coloured by it in yellow shades with good fastness to migration and light. When incorporated in varnishes, the pigment has very good fastness to light, weathering and overstripe bleeding.

EXAMPLES 2–5

The procedure of Example 1 is repeated, substituting the following diamines for 2,5-dichloro-1,4-phenylenediamine:

| Example | |
|---|---|
| 2 | 2-chloro-5-methyl-1,4-phenylenediamine |
| 3 | 2,5-dimethyl-1,4-phenylenediamine |
| 4 | 2-chloro-5-methoxy-1,4-phenylenediamine |
| 5 | 2,5-dibromo-1,4-phenylenediamine |

Yellow pigments are also obtained with the same good fastness properties. To obtain optimum fastness properties, these pigments are suspended in 100 ml of dimethyl formamide, heated with stirring to 100° C, filtered hot and washed with dimethyl formamide and water.

EXAMPLE 6

With stirring, 15.5 g of 1-amino-3-imino-isoindolenine and 3.5 g of 2,5-dichloro-1,4-phenylenediamine are refluxed in 100 ml of methanol. The precipitate is filtered off, washed with methanol and water and dried. The product is suspended in 100 ml of dimethyl formamide, heated with stirring to 100° C and filtered hot and then dried to yield 7.2 g of the pigment of Example 1.

EXAMPLE 7

The procedure of Example 1 is repeated, substituting 14 g of 1-amino-3-imino-5,6-dichloro-isoindolenine for 1-amino-3-imino-isoindolenine. A reddish yellow pigment is obtained.

EXAMPLE 8

A mixture of 6.7 g of phthalodinitrile, 4.42 g of 2,5-dichloro-1,4-phenylenediamine and 0.54 g of sodium methylate is heated to 50° C, with stirring, in 50 ml of methanol. This temperature is kept until a clear solution forms, which is then cooled. A precipitate gradually separates. After 48 hours, the batch is acidified with 5 ml of acetic acid and filtered. The filter cake is dried to yield 5.2 g of pigment whose infra-red spectrum accords with that of the product of Example 1.

EXAMPLE 9

65 parts of stabilised polyvinyl chloride, 35 parts of dioctyl phthalate and 0.2 part of the pigment obtained according to Example 1 are stirred together and then rolled to and for 7 minutes at 140° C in a two roll moll. A brilliant yellow sheet of very good fastness to light and migration is obtained.

EXAMPLE 10

10 g of titanium dioxide and 2 g of the pigment obtained in Example 1 are ground for 48 hours in a ball mill with 88 g of a mixture of 26.4 g of coconut alkyd resin, 24 g of melamine/formaldehyde resin (50% solids content), 8,8 g of ethylene glycol monomethyl ether and 28.8 g of xylene. The resultant varnish is sprayed onto an aluminium sheet, predried for 30 minutes at room temperature and then stoved for 30 minutes at 120° C. A brilliant yellow finish of good colour strength is obtained which is characterised by very good fastness to overstripe bleeding, light and weathering.

EXAMPLE 11

(Acrylic Resin Stoving Enamel)

4 parts of the finely divided pigment of Example 1 are stirred into 20 parts of a solvent of the following composition:
- 50 parts of Solvesso 150 (mixture of aromatic hydrocarbons)
- 15 parts of butyl acetate
- 5 parts of Exkin II (levelling agent based on ketoxime)
- 25 parts of methyl isobutyl ketone
- 5 parts of silicone oil (1% in Solvesso 150).

After complete dispersion has been attained (app. 15–60 minutes depending on the nature of the stirrer), the following binders are added:
- 48.3 parts of Baycryl L 530 (acrylic resin) (51% in xylene/butanol 3:1) and
- 23.7 parts of Maprenal TTX (melamine resin) (55% in butanol).

After it has been homogenised briefly, the varnish is applied by conventional methods, such as spraying or immersion or coil coating for the continuous coating of metal sheets, and stoved (stoving for 30 minutes at 130° C). The resultant yellow finishes are characterised by very good levelness, high gloss and excellent fine distribution of the pigment as well as by excellent weather fastness properties.

I claim:

1. An iminoisoindolenine pigment of the formula

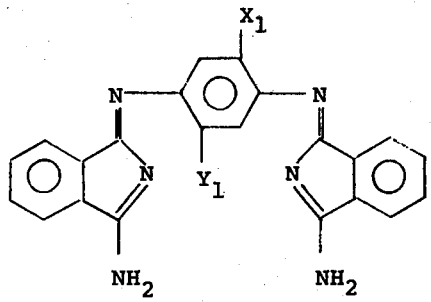

wherein X and $Y_1$ are chloro or bromo.

2. The compound according to claim 1 of formula

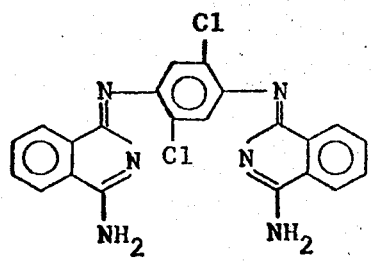

3. The compound according to claim 1 of the formula

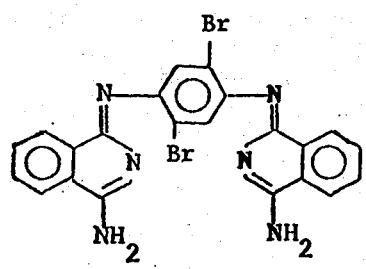

* * * * *